(12) United States Patent
Hell et al.

(10) Patent No.: US 9,835,838 B2
(45) Date of Patent: Dec. 5, 2017

(54) SCANNING LUMINESCENCE LIGHT MICROSCOPE WITH GRATINGS OF LUMINESCENCE INHIBITION LIGHT AND FURTHER LIGHT

(71) Applicant: Max-Planck-Gesellschaft zur Foerderung der Wissenschaften e.V.[D]], Munich (DE)

(72) Inventors: Stefan W. Hell, Goettingen (DE); Andriy Chmyrov, Munich (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 43 days.

(21) Appl. No.: 15/180,491

(22) Filed: Jun. 13, 2016

(65) Prior Publication Data
US 2016/0363751 A1 Dec. 15, 2016

(30) Foreign Application Priority Data
Jun. 11, 2015 (DE) .................. 10 2015 109 305

(51) Int. Cl.
*G01N 21/64* (2006.01)
*G02B 21/00* (2006.01)
(Continued)

(52) U.S. Cl.
CPC ..... *G02B 21/0076* (2013.01); *G01N 21/6458* (2013.01); *G02B 21/0032* (2013.01);
(Continued)

(58) Field of Classification Search
CPC .................. G01N 21/6458; G02B 21/0076
See application file for complete search history.

(56) References Cited

U.S. PATENT DOCUMENTS 7,646,481 B2   1/2010   Dyba et al.
7,903,247 B2   3/2011   Dyba et al.
(Continued)

FOREIGN PATENT DOCUMENTS

DE   10 2006 009 833 B4   1/2009
WO      2006/058187 A2    6/2006
(Continued)

OTHER PUBLICATIONS

Chmyrov et al., "Nanoscopy with more than 100,000 'doughnuts'," Nature Methods, vol. 10 (8), published Aug. 2013, pp. 737-742.*
(Continued)

*Primary Examiner* — Casey Bryant
(74) *Attorney, Agent, or Firm* — Thomas | Horstemeyer, LLP (57) ABSTRACT

A scanning luminescence light microscope for spatial high resolution imaging a structure marked with a luminescent marker comprises a light source for luminescence inhibition light and for further light; a light shaping and aligning device; and a detector registering luminescence light emitted by the luminescent marker. The device, by means of two optical gratings and an objective lens, forms two crossing line gratings of the luminescence inhibition light, and two crossing line gratings of the further light so that local intensity minima of an overall intensity distribution of the luminescence inhibition light are delimited in at least two directions, and that local intensity maxima or local intensity minima of an overall intensity distribution of the further light coincide with the local intensity minima of the luminescence inhibition light. Further, the device moves the overall intensity distributions of the further light and the luminescence inhibition light to scan the structure.

20 Claims, 4 Drawing Sheets

(51) Int. Cl.
  *G02B 27/42* (2006.01)
  *G02B 27/58* (2006.01)
  *G01N 21/63* (2006.01)

(52) U.S. Cl.
  CPC ..... *G02B 21/0036* (2013.01); *G02B 21/0072* (2013.01); *G02B 27/425* (2013.01); *G01N 2021/633* (2013.01); *G01N 2021/6463* (2013.01); *G01N 2201/0635* (2013.01); *G02B 27/58* (2013.01)

(56) References Cited

U.S. PATENT DOCUMENTS 9,719,928 B2 * 8/2017 Hell .................. G01N 21/6458
2007/0268583 A1 11/2007 Dyba et al.

FOREIGN PATENT DOCUMENTS

WO    2006/127692 A2   11/2006
WO    2012/069076 A1   5/2012

OTHER PUBLICATIONS

Lavoie-Cardinal et al., "Two-Color RESOLFT Nanoscopy with Green and Red Fluorescent Photochromic Proteins," Chem Phys Chem 2014, vol. 15, pp. 655-663.*
Grotjohann et al., "rsEGFP2 enables fast RESOLFT nanoscopy of living cells," eLIFE Sciences: Biophysics and Structural Biology, published Dec. 31, 2012, pp. 1-14.*
P. Bingen, et al., "Parallelized STED Fluorescence Nanoscopy", Opt. Express, vol. 19, 23716-23726 (2011).

* cited by examiner

SCANNING LUMINESCENCE LIGHT MICROSCOPE WITH GRATINGS OF LUMINESCENCE INHIBITION LIGHT AND FURTHER LIGHT

CROSS REFERENCE TO RELATED APPLICATIONS

The present invention claims priority to German Patent Application No. DE 10 2015 109 305.7, filed Jun. 11, 2015, and entitled "Rasterlumineszenzlichtmikroskop mit Gittern aus Lumineszenzverhinderungslicht und weiterem Licht".

FIELD

The present invention relates to a scanning luminescence light microscope for spatial high resolution imaging a structure in a sample, the structure comprising a luminescent marker.

More particular, the present invention relates to such a scanning luminescence light microscope comprising a light source for luminescence inhibition light and for further light, a light shaping and aligning device, and a detector, the detector registering luminescence light emitted by the luminescent marker out of intensity minima of an intensity distribution of the luminescence inhibition light.

BACKGROUND

A method of spatial high resolution imaging a structure of a sample, the structure comprising a luminescent marker, is known as STED (Stimulated Emission Depletion) scanning luminescence light microscopy. Here, the sample is at first subjected to focused excitation light exciting the luminescent marker out of an excitable electronic ground state into a luminescent electronic state. Then, the sample is subjected to an intensity distribution of emission stimulation light stimulating the excited luminescent marker for emission of light at the wavelength of the emission stimulation light, i.e. at another wavelength as that one of the luminescence light, and thus de-exciting the excited luminescent marker back into its ground state. The intensity distribution of the emission stimulation light has a local intensity minimum. If the emission stimulation light has de-excited the excited luminescent marker by stimulated emission everywhere outside this local intensity minimum, luminescence light afterwards emitted out of the area of the intensity distribution of the emission stimulation light may only come out of the intensity minimum. Thus, this luminescence light may be assigned to the position of the intensity minimum within the sample. If the minimum is a null or zero point of an interference pattern of the emission stimulation light, for example, increasing the intensity of the emission stimulation light decreases the dimensions of the intensity minimum within which the emission stimulation light does not completely de-excite the excited luminescent marker, i.e. not up a saturation of this de-excitation. By increasing the intensity of the emission stimulation light, the dimensions of the intensity minimum may particularly be made smaller than Abbe's diffraction limit at the wavelength of the excitation light and the luminescence light which delimits the spatial resolution in exciting the sample with the focused excitation light and in imaging the structure of the sample emitting the luminescence light onto an image sensor.

A further method of spatial high resolution imaging a structure of a sample, the structure comprising a luminescent marker, is known as GSD (Ground State Depletion) scanning luminescence light microscopy. In this known method, the sample, prior to being subjected to focused excitation light, is subjected to an intensity distribution of luminescence inhibition light comprising a local intensity minimum, the luminescence inhibition light transferring the luminescent marker into a long-living electronic dark state, like for example a triplet state, out of which it is not excited by the excitation light into a luminescent electronic state. Everywhere outside the intensity minimum of the intensity distribution of the luminescence inhibition light this transfer into the dark state is driven up to saturation. I.e. only in the intensity minimum of the intensity distribution of the luminescence inhibition light, the luminescent marker, after application of the luminescence inhibition light, is still in its electronic ground state out of which it is excited by the excitation light into the luminescent state. Luminescence light emitted by the luminescent marker after the excitation with the excitation light thus comes out of the intensity minimum of the intensity distribution of the luminescence inhibition light and may thus be assigned to the position of the intensity minimum within the sample independently on the spatial resolution in exciting the sample and in imaging the sample onto the detector used.

Both STED and GSD scanning luminescence light microscopy belong to RESOLFT (Reversible Saturable Optical Fluorescence Transitions) scanning luminescence light microscopy. A further method belonging to RESOLFT scanning luminescence light microscopy makes use of a so-called switchable luminescent marker for spatial high resolution imaging of a structure of a sample comprising the luminescent marker. By means of luminescence inhibition light, the switchable luminescent marker is switched out of a first conformation state in which it is effective as a luminescent marker into a second conformation state in which it is not effective as a luminescent marker. Thus, the switchable luminescent marker, in its second conformation state, at least by means of excitation light which is suitable for exciting the switchable luminescent marker its first conformation state, is not excitable into a luminescent electronic state out of which it emits the luminescence light being registered. With a sufficient long lifetime of the second conformation state, only comparatively low light intensities are required to drive this switching up to saturation everywhere outside a local intensity minimum of an intensity distribution of the luminescence inhibition light. Further, there is no significant danger that the luminescent marker transferred into its second conformation state is bleached, as it does not respond to the luminescence inhibition light and the excitation light in its second conformation state.

In all variants of RESOLFT scanning luminescence light microscopy, only luminescence light is registered, which comes out of an area of the sample corresponding to the position of the local intensity minimum of the luminescence inhibition light in the sample. For imaging a larger area of the sample, the sample is scanned with the local intensity minimum of the luminescence inhibition light. From the luminescence light registered during scanning, an image of the larger area of the sample can be generated.

P. Bingen, M. Reuss, J. Engelhardt, and S. W. Hell: "Parallelized STED fluorescence nanoscopy", Opt. Express 19, 23716-23726 (2011) describe an STED scanning fluorescence light microscope in which an intensity distribution of emission stimulation light is composed of four partial intensity distributions arranged side by side. Each of the four partial intensity distributions comprises a local intensity minimum delimited in two dimensions. Further, each of the four partial intensity distributions of the emission stimulation light is superimposed with a partial intensity distribution of excitation light which comprises an intensity maximum at the location of the intensity minimum of the emission stimulation light. The partial intensity distributions are generated in that beams of the emission stimulation light and of the excitation light which are aligned on a common optical axis pass through two Wollaston prisms arranged one behind the other. The Wollaston prisms divide the beams into partial beams which, in pairs of one partial beam of stimulation light and one partial beam of excitation light, propagate in four slightly different directions. These four pairs of partial beams pass through a segmented chromatic phase plate which selectively deforms the wavefronts of the partial beams of the luminescence inhibition light so that these partial beams, when all partial beams are afterwards focused into the sample, form the partial intensity distributions with the intensity minima. Due to the four different directions of the partial beams, the partial intensity distributions are arranged at distances within the sample and define four similar local intensity minima. The luminescence light emitted out of the four local intensity minima is spatially separated and registered. By simultaneously scanning the sample with the four intensity minima of the luminescence inhibition light arranged at distances, the time required for imaging the structure of interest is reduced to a quarter as compared to imaging the structure only using one intensity minimum.

WO 2006/127692 A2 discloses a method of high resolution imaging a structure of a sample, the structure comprising a phototransformable optical label (PTOL), which is also based on the RESOLFT concept. By means of a pulse of activation light, the PTOL is transferred out of an inactive state into an active state. In the active state (in contrast to the inactive state) the PTOL may be excited by excitation light for the emission of luminescence light. The sample is subjected to an intensity distribution of the activation light in form of an activation point grating of point-shaped intensity maxima. In the areas with relevant intensity of the activation light, particularly within the intensity maxima of the activation light, the PTOL is activated. Afterwards, i.e. already prior to subjecting the sample to the excitation light, the sample is subjected to a pulse of deactivation light which transfers the PTOL back into its inactive state. The intensity distribution of the deactivation light is formed as a deactivation point grating which is similar to the activation grating. In the deactivation grating, however, intensity minima of the deactivation light are provided at the grating points which are surrounded by shells of higher intensity of the deactivation light. As the deactivation grating is superimposed with the activation grating in such a way that each intensity maximum of the activation light coincides with one intensity minimum of the deactivation light, the PTOL, everywhere outside of the intensity minima of the deactivation light, is transferred back into its inactive state. When the sample is afterwards subjected to an excitation point grating of excitation light which, in the areas of the local maxima of the activation point grating also has local intensity maxima, the PTOL is only excited for the emission of luminescence light in those areas of the intensity minima of the deactivation point grating in which the PTOL is still in its active state. Due to the point grating-shaped illumination with the activation, the deactivation and the excitation light, a parallelized high resolution full image of the structure of the sample is obtained. With regard to the generation of the point grating-shaped intensity distributions, WO 2006/127692 A2 refers to WO 2006/058187 A2.

According to WO 2006/058187 A2, a two- or three-dimensional point grating-shaped intensity distribution in a sample with local intensity maxima at the grating points is generated in that three or four beams of coherent light with different propagation directions are superimposed within the sample such as to form an interference pattern. By adjusting the phases of the individual beams of light it shall be possible to generate local intensity minima at the grating points which are enclosed by areas of higher intensity. Adjusting the phases is achieved by means of a movable reflector, an optical phase modulator or a spatial light modulator (SLM). For generating the point gratings of the activation, the deactivation and the excitation light, pluralities of coherent light beams with different propagation directions are superimposed within the sample so that the desired intensity distribution results from optical interference. According to WO 2006/058187 A2, the point grating-shaped intensity distributions may be used in an STED scanning fluorescence microscope. Here, the sample is subjected to a point grating-shaped intensity distribution of pulsed excitation light with local intensity maxima at the grating points. The excitation light excites a fluorescent marker in the sample for the emission of fluorescence light. Additionally, the sample is subjected to a point grating-shaped intensity distribution of pulsed emission stimulation light having a plurality of local intensity minima. The emission stimulation light, by means of stimulated emission, transfers the fluorescent marker back into its ground state. For generating the intensity distribution of the emission stimulation light with local intensity minima at the grating points which are each surrounded by an area of higher intensity, according to WO 2006/058187 A1, a plurality of similar sub-gratings of the emission stimulation light are generated and superimposed within the sample. Each sub-grating is generated as a three-dimensional point grating with local intensity maxima at the grating points. For each sub-grating three or four beams of light are superimposed whose phases are adjusted with regard to each other in such a way that the respective sub-grating has the desired symmetry and periodicity within the sample. Adapting the phases of the beams of light and thus shifting the sub-gratings with regard to each other, the gratings are then superimposed within the sample in such a way that they all together generate a point grating of local intensity minima. The intensity maxima of the sub-gratings are arranged at an offset in different directions with regard to the intensity minima of the overall grating. The shape of the intensity minima is defined by the relative arrangement of the intensity maxima delimiting the intensity minima. Due to the delimitation of the intensity minima by means of point-shaped or spherical intensity maxima, the intensity minima have no round shape but different extensions in different directions.

A further scanning luminescence light microscope for spatial high resolution examination of samples is disclosed in DE 2006 009 833 B4. Here, means for providing four beams of light of luminescence inhibition light which are coherent in pairs and means for focusing the four beams of light into the pupil of an objective are provided to generate superimposed standing waves in two directions, i.e. two crossing line gratings. The means for providing the four beams of light which are coherent in pairs, for example, include a holographic grating within the beam path. Adjustable retroreflectors are provided for a path length adjustment between the pairs of coherent light beams. An additional light source, like for example for switching or excitation light, illuminates the entire field of view of this known scanning luminescence light microscope.

There is still a need of a scanning luminescence light microscope for spatial high resolution imaging of a structure of a sample comprising a luminescent marker in which the intensity distributions of the luminescence inhibition light and the further light are optimized even over a high number of intensity minima of the luminescence inhibition light.

SUMMARY OF THE INVENTION

The present invention relates to a scanning luminescence light microscope for spatial high resolution imaging a structure in a sample, the structure comprising a luminescent marker. The microscope comprises a light source, a light shaping and aligning device including an objective lens of the microscope; and a detector. The light source provides luminescence inhibition light and further light differing from the luminescence inhibition light. The light shaping and aligning device forms, from two non-coherent beams of the luminescence inhibition light, by means of two optical gratings, two pairs of coherent partial beams of the luminescence inhibition light and to focus and superimpose the two pairs of partial beams of the luminescence inhibition light by means of the objective so that the two pairs of partial beams of the luminescence inhibition light form two crossing line gratings of the luminescence inhibition light in the area of the sample, each of the two crossing line gratings of the luminescence inhibition light comprising a plurality of intensity minima delimited in one direction so that an intensity distribution of the luminescence inhibition light in the sample comprises a two-dimensional array of local intensity minima which are delimited in at least two directions. At least one beam of the further light enters the light shaping and aligning device together with one of the two beams of the luminescence inhibition light so that the light shaping and aligning device, from the beam of the further light, by means of one of the optical gratings, forms two coherent partial beams of the further light and focuses and superimposes the partial beams of the further light by means of the objective so that the partial beams of the further light form a line grating of the further light in the area of the sample which comprises a plurality of intensity maxima delimited in one direction and intensity minima extending in parallel to the local intensity minima of one of the line gratings of the luminescence inhibition light. The light shaping and aligning device aligns the line grating of the further light with regard to the one of the line gratings of the luminescence inhibition light in such a way that the local intensity maxima or the local intensity minima of the further light coincide with the intensity minima of the luminescence inhibition light. The light shaping and aligning device moves the intensity distributions of the further light and the luminescence inhibition light with regard to the sample to scan an area of interest of the sample with the intensity minima of the intensity distribution of the luminescence inhibition light. The detector registers the luminescence light emitted out of the individual intensity minima of the intensity distribution of the luminescence inhibition light separately for each of the intensity minima and for each position of each of the intensity minima within the sample Other features and advantages of the present invention will become apparent to one with skill in the art upon examination of the following drawings and the detailed description.

It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

In the scanning luminescence light microscope according to the invention, the intensity of the luminescence light registered for the individual intensity minima of the intensity distribution of the luminescence inhibition light is a measure of the concentration of the luminescent marker at the respective position of the respective intensity minimum within the sample. By scanning the sample with the intensity minima of the intensity distribution of the luminescence inhibition light and registering the luminescence inhibition light for each position of the intensity minima, the distribution of the luminescent marker within the sample is captured, and thus the structure comprising the luminescent marker is imaged.

The structure of interest in the sample may comprise the luminescent marker by nature, i.e. per se. The structure of interest in the sample may, however, also be artificially marked with the luminescent marker. The artificial marking of the structure with the luminescent marker may, for example, be achieved by so-called antibody dyeing, i.e. by coupling the luminescent marker via an immunoreaction, or by means of a genetic engineering modification which results in the luminescent marker being expressed together with the structure of interest; one example of suitable luminescent markers being fluorescent proteins.

The luminescent marker marking the structure of interest in the sample may particularly be a fluorophore. In this case, the luminescence light which is emitted by the luminescent marker is fluorescence light. The luminescence light may, however, also be emitted by the luminescent marker based on other processes than fluorescence. One example of such another process is autoluminescence, i.e. purely thermally excited luminescence. Often, the luminescent marker, however, will be excited for the emission of luminescence light by means of excitation light. This excitation light may be the further light differing from the luminescence inhibition light, which is additionally provided by the light source of the scanning luminescence light microscope. Generally, the further light may also have another function. For example, the further light may switch a luminescent marker in form of a switchable protein into a state in which it is generally capable of fluorescence, and in which it is then excited for emission of luminescence light in form of fluorescence light by means of additional excitation light. Here, the additional excitation light may be an additional component of the further light having another wavelength than the component of the further light switching the luminescent marker into its state capable of fluorescence. Then, the intensity maxima of both components of the further light may coincide with the intensity minima of the fluorescence inhibition light. In a further example, the further light switches a luminescent marker in form of a switchable protein into a protected state in which luminescent marker is protected against bleaching caused by the luminescence inhibition light. Then, the intensity minima at least of this component of the further light switching into the protected state may coincide with the intensity minima of the fluorescence inhibition light. Also n this latter embodiment, additional excitation light may excite the luminescent marker for emission of luminescence light in form of fluorescence light and make up an additional component of the further light having another wavelength. In this case, the intensity maxima of the excitation component of the further light will coincide with the intensity minima of both the luminescence inhibition light and the switching component of the further light.

Generally, the further light may have several functions and it may then comprise several components of different wavelengths. Here, the intensity minima and/or the intensity maxima of the individual components may coincide with the intensity minima of the luminescence inhibition light. Thus, the intensity maxima of one component may even coincide with the intensity minima of another component of the further light.

The luminescence inhibition light has such an effect on the luminescent marker that, within the area of influence of the luminescence inhibition light, the luminescent marker is not capable of the emission of luminescence light. The mechanisms of luminescence inhibition on which this effect is based may be very different. For example, the luminescence inhibition light may de-excite the previously excited luminescent marker by means of stimulated emission. In another embodiment, the luminescence inhibition light may transfer the luminescent marker into a dark state in which no excitation for emission of fluorescence light and/or out of which no emission of fluorescence light is possible. This dark state may, for example, be an electronic state, particularly a triplet state, or a non-luminescent conformation state, like for example a non-luminescent conformation state of a switchable protein.

If intensity minima or local intensity minima of the intensity distribution are mentioned here, particularly nulls or zero points of the intensity distribution of the respective light are meant. These zero points may be true zero points within which the intensity of the respective light in fact goes down to zero but also such zero points in which the intensity of the respective light, due to non-ideal optical conditions, does not completely, i.e. only essentially, go down to zero.

If the dimensions or extensions of intensity minima or local intensity minima are mentioned here, these dimensions or extensions particularly relate to the dimensions of the area or volume within which the respective light does not achieve its desired effect, like for example luminescence inhibition, up to saturation.

If it is mentioned here that the luminescence light is registered for each of the individual intensity minima of the intensity distribution of the luminescence inhibition light and for each position of the intensity minima, this particularly means a separate registration for the individual intensity minima and their different positions. This, however, does not exclude that, with closely neighboring intensity minima, luminescence light emitted out of the one intensity minimum is also registered when one (only) wants to register luminescence light out of the other intensity minimum. Such a cross talk of the luminescence light between the intensity minima is not critical as long as it is irrelevant per se, i.e. without effect on the image of interest of the structure comprising the luminescent marker, or if it can be separated when evaluating the luminescence light.

In the scanning luminescence light microscope according to the invention, the intensity distribution of the luminescence inhibition light is generated by means of non-coherent superposition of two partial intensity distributions in form of crossing line gratings. Here, each of the line gratings has a plurality of local intensity minima which, in contrast to the at least two-dimensionally delimited local intensity minima of the overall intensity distribution of the luminescence inhibition light, are only delimited in one dimension or direction. Two or even more of these line gratings are superimposed to generate the overall intensity distribution. For generating an overall intensity distribution with intensity minima which are delimited in two dimensions, it is sufficient to superimpose two line gratings with intensity minima delimited in one dimension. If an overall intensity distribution with intensity minima delimited in three dimensions is to be generated, at least three line gratings with intensity minima delimited in one dimension are needed. In the scanning luminescence light microscope according to the invention, at least the pairs of coherent partial beams used for forming two of the crossing line gratings are formed by means of optical gratings.

The number of the generated intensity minima of the overall intensity distribution which are delimited in more than one dimension depends on the number of the intensity minima of the superimposed line gratings. If, for example, two line gratings are superimposed which each comprise three intensity minima delimited in one dimension and overlapping in the superposition, the resulting intensity distribution comprises nine local intensity minima delimited in two dimensions. I.e., the number of the intensity minima of the intensity distribution results from a multiplication of the number of the superimposed intensity minima of the line gratings delimited in one dimension. Thus, the superposition of the line gratings is no simple adding up of multi-dimensionally delimited local intensity minima. Correspondingly, an intensity distribution of the luminescence inhibition light comprising a high number of multi-dimensionally delimited intensity minima may be generated with the method according to the invention in a simple way. Thus, the present invention allows for quickly scanning the entire sample with a high number of multi-dimensionally delimited intensity minima.

Due to the fact that the line gratings of the luminescence inhibition light are formed by means of optical gratings, the local intensity minima of each of the line gratings are essentially equidistant and parallel. Thus, the intensity minima of the resulting intensity distribution of the luminescence inhibition light are arranged in a uniform pattern or raster, and the sample may particularly efficiently be scanned with the intensity minima. In the scanning luminescence light microscope according to the invention, both light transmissive and light reflective optical gratings may be used.

If the line gratings of the luminescence inhibition light comprising the only one-dimensionally delimited intensity minima, in creating the intensity distribution with the multi-dimensionally delimited intensity minima, are superimposed in such a way that the one-dimensionally delimited intensity minima of the different line gratings are orthogonal to each other, the generated overall intensity distribution comprises a maximum density of multi-dimensionally delimited intensity minima. Further, each of the multi-dimensionally delimited intensity minima, in the directions of the sequence of the one-dimensional delimited intensity minima of the line gratings of the luminescence inhibition light, is narrowly delimited by neighboring local maxima of these line grating, whereas, in the diagonal directions, the delimitation of the multi-dimensionally delimited intensity minima is less narrow but effected by the superimposed local intensity maxima of the line gratings and thus by higher absolute intensities of the luminescence inhibition light. As a result, there are same effective dimensions or extensions of the multi-dimensionality limited intensity minima in all directions.

Particularly, in a plane defined by the directions of the one-dimensional delimitations, each intensity minimum of the overall intensity distribution of the luminescence inhibition light is enclosed by a line along which the intensity of the luminescence inhibition light alternatingly increases from the single intensity of the local maxima of the individual line gratings to twice this intensity in the crossing points of the local maxima of the individual line gratings and then drops down to the single intensity again. If the line gratings are orthogonally superimposed, all points on the line in which the double intensity is reached have a maximum distance to the local minimum, whereas all points of the single intensity have a minimum distance to the local minimum. Thus, the multi-dimensionally delimited local intensity minima of the resulting overall intensity distribution are essentially circular in the two-dimensional case and essentially spherical in the three-dimensional case.

Whereas, in the scanning luminescence light microscope according to the invention, an interference of coherent partial beams of the luminescence inhibition light formed by optical gratings is used to achieve small distances and dimensions of the one-dimensionally delimited intensity minima, interference effects would affect the generation of the desired overall intensity distribution of the luminescence inhibition light in superposition of the individual line gratings. Thus, these negative interference effects are avoided in that the line gratings are non-coherently superimposed in forming the overall intensity distribution, i.e. the luminescence inhibition light of the one line grating is not coherent with regard to the luminescence inhibition light of the other line grating within the sample. This is, for example, achieved in that the luminescence inhibition light for the two line gratings is provided by two separate partial light sources. If the luminescence inhibition light for the line gratings is provided by one and the same partial light beam, the non-coherent superposition may be achieved in that the light paths of the luminescence inhibition light for the different line gratings differ in length from the partial light source to the sample by more than their coherence length. A non-coherent superposition of the line gratings in the sample may also be ensured in that luminescence inhibition light of different wavelengths or different polarizations is used for the different line gratings.

The desired result that the line gratings are non-coherently superimposed within the sample may also be realized in that the sample is subjected to the line gratings in a temporal sequence, i.e. one after the other. Preferably, the temporal sequence is short as compared to the temporal sequence of all other steps carried out in using the scanning luminescence light microscope according to the present invention. The temporal sequence of the line gratings may have the result that the sample, at each point in time, is at maximum subjected to one of the line gratings. Then, at no point in time of the sequence, the double intensity of the luminescence inhibition light is present at the crossing points of the line gratings or circular or spherical minima of the intensity distribution of the luminescence inhibition light are visible in the sample. However, the effective intensity minima of the overall or temporally averaged intensity distribution of the luminescence inhibition light, in which the luminescent marker is not inhibited with regard to the emission of luminescence light by means of the luminescence inhibition light, are nevertheless circular or spherical. A temporal sequence of the line gratings and their result that at no point in time the double intensity is present at the crossing points of the line gratings may reduce the danger of a photochemical bleaching of the luminescent marker due to being subjected to the luminescence inhibition light, particularly if this danger non-linearly depends on the intensity of the luminescence inhibition light, like in case of a multi-photon photochemical bleaching process.

For obtaining the measurement signal, I.e. luminescence light, out of the minima of the intensity distribution of the luminescence inhibition light, only, and thus for high spatial resolution imaging the structure of interest in the sample, subjecting the sample to the intensity distribution of the luminescence inhibition light may be sufficient. Then, no additional application of excitation light for exciting the luminescent marker for the emission of luminescence light is necessary. This may be the case, if the luminescent marker is autoluminescent or if the luminescence inhibition light only transfers the luminescent marker in a state out of which the luminescent marker does not emit luminescence light at higher intensities but even excites the luminescent marker for the emission of luminescence light at lower intensities as they are present in the intensity minima of the luminescence inhibition light. These properties of the luminescent marker with regard to the intensity of the luminescence inhibition light may, for example, be used in a GSD embodiment of the scanning luminescence light microscope disclosed here.

In the scanning luminescence light microscope according to the present invention, however, the further light differing from the luminescence inhibition light is additionally applied to the sample.

At least one beam of this further light is split up in partial beams by means of one of the same optical gratings which are used for forming one of the pairs of coherent partial beams of the luminescence inhibition light. Further, these partial beams of the further light are focused and superimposed in the sample so that a line grating of the further light is formed within the sample by means of the same objective lens which is also used for focusing and superimposing the partial beams of the luminescence inhibition light. Here, it is an advantage that, despite of chromatic errors of the objective lens, the parallel line gratings in the sample all have a same grating constant only depending on the grating constant of the optical grating but not depending on the wavelength of the luminescence inhibition light and the further light. By means of the same optical gratings, the partial beams of light of a longer wavelength are deflected at a higher deflection angle than the partial beams of light of a shorter wavelength, and this larger defection angle exactly compensates for the influence of the wavelength of the light on the grating constant of the line grating formed when focusing and superimposing the partial beams of the light in the sample. These facts allow for adjusting the line gratings of the luminescence inhibition light and the further light in such a way that the intensity minima or the intensity maxima of the line grating of the further light independently on its wavelength exactly coincide with the intensity minima of the line grating of the luminescence inhibition light over several periods of the line gratings.

Thus, for example, the intensity of excitation light provided as the further light and exciting the luminescent marker for the emission of luminescence light may be concentrated in the intensity minima of at least one of the line gratings of the luminescence inhibition light. In another embodiment, the intensity of activation light provided as the further light and switching the luminescent marker into an active state out of which it is excitable for the emission of luminescence light may also be concentrated in the intensity minima of at least one of the line gratings of the luminescence inhibition light.

Vice versa, the intensity of deactivation light switching the luminescent marker into an inactive state in which it is not excitable for the emission of luminescence light and provided as the further light in addition to stimulation light which is provided as the luminescence inhibition light may be concentrated outside the intensity minima of at least one line grating of the luminescence inhibition light so that the intensity minima of these line gratings of the luminescence inhibition light and the further light coincide. In this case, the effective dimensions of the intensity minima out of which the luminescence light may still be emitted are delimited by both the luminescence inhibition light and the further light. On the other hand, the further light avoids that the luminescent marker, in its active state, is subjected to high intensities of the luminescence inhibition light which are associated with a high risk of bleaching.

In preferred embodiments of the scanning luminescence light microscope according to the invention, not only one beam of the further light enters the light shaping and aligning device together with one of the two beams of the luminescence inhibition light but the further light also comprises two non-coherent beams each entering the light shaping aligning device together with one of the two beams of the luminescence inhibition light. Thus, the light shaping and aligning device forms two pairs of coherent partial beams of the further light from the two beams of the further light by means of the same optical gratings which also split up the beams of the luminescence inhibition light. The partial beams of the further light are then focused and superimposed by means of the same objective lens as the partial beams of the luminescence inhibition light so that they form two line gratings of the further light crossing within the sample. Each of the these line gratings comprises a plurality of one-dimensionally delimited local intensity minima and maxima which run in parallel to the local intensity minima of one of the line gratings of the luminescence inhibition light. Thus, an overall intensity distribution of the further light in the sample comprises a two-dimensional array of similar, at least two-dimensionally delimited local intensity maxima and intensity minima. The light shaping and aligning device aligns this overall intensity distribution of the further light with regard to the overall intensity distribution of the luminescence inhibition light in such a way that the local intensity maxima or the local intensity minima of the overall intensity distribution of the further light coincide with the local intensity minima of the overall intensity distribution of the luminescence inhibition light. If the local intensity minima of the overall intensity distribution of the luminescence inhibition light are not only two-dimensionally but even three-dimensionally delimited and if at least three non-coherent beams of the luminescence inhibition light are split up by optical gratings into pairs of coherent partial beams of the luminescence inhibition light, three non-coherent beams of the further light may also be used and split up into pairs of coherent partial beams, which are superimposed in the sample to form line gratings together with the beams of the luminescence inhibition light. In this case, the same gratings and the same objective lens may be used for the third beam of the further light which are also used for splitting up the third beam of the luminescence inhibition light and for focusing and superimposing its partial beams with the sample.

Whether the local intensity maxima or the local intensity minima of the line grating of the further light coincide with the parallel local minima of the respective line grating of the luminescence inhibition light is a matter of relative adjustment of the optical path lengths of the partial beams of each pair of coherent partial beams of the further light with regard to the optical path lengths of the partial beams of the pair of the coherent partial beams of the luminescence inhibition light formed by means of the same optical grating. Here, the optical path lengths from the respective optical grating up to the respective line gratings of the further light and the luminescence inhibition light are relevant. In the scanning luminescence light microscope, these optical path lengths are defined by the light shaping and aligning device. For this purpose, for example, a mirror which only reflects one partial beam of each pair of the coherent partial beams may be shifted to vary the optical path lengths of the partial beams reflected. This variation has the same effect on the absolute optical path length of both reflected partial beams. With different wavelengths of the further light and the luminescence inhibition light, however, this variation nevertheless also alters the relative wavelengths, i.e. the relative phases between the two partial beams of the further light and the two partial beams of the luminescence inhibition light, and thus the relative positions of the intensity maxima or intensity minima of the line grating of the further light with regard to the parallel intensity minima of the line grating of the luminescence inhibition light.

In a particular embodiment of the scanning luminescence light microscope according to the invention, the light shaping and aligning device comprises at least one optical element selectively arranged within one or both of one of the beam paths of one of the partial beams of one of the pairs of coherent partial beams of the further light and of one of the partial beams of the pair of the partial beams of the luminescence inhibition light formed by means of the same optical grating. The purpose of this optical element is the relative adjustment of the optical path lengths of the one pair of coherent partial beams of the further light and the pair of coherent partial beams of the luminescence inhibition light formed by means of the same optical grating. If the optical element is interchangeable, different optical elements may be provided to either let the local intensity maxima of the intensity distribution of the further light or let the local intensity minima of the intensity distribution of the further light coincide with the local intensity minima of the intensity distribution of the luminescence inhibition light. Further, different combinations of wavelengths of the further light and the luminescence inhibition light may be covered by different optical elements. Particularly, the optical element may be selected from chromatic and birefringent optical elements by which the desired phase relation between the two pairs of partial beams of the further light and the luminescence inhibition light are adjusted.

Generally, the optical element may also be designed such that it adjusts the optical path lengths of the partial beams of each pair of coherent partial beams of the further light and the optical path lengths of the partial beams of the pair of coherent partial beams of the luminescence inhibition light formed by means of the same optical grating for different wavelengths of at least one of the further light and of the luminescence inhibition light in such a way that the local intensity maxima or the local intensity minima of the line grating of the further light coincide with the parallel local intensity minima of the respective line grating of the luminescence inhibition light as desired. In this way, interchanging the optical element becomes unnecessary at least for various combinations of the wavelengths of the further light and the luminescence inhibition light for which the optical element is designed.

Instead of adjusting the optical path lengths between the respective optical grating and the line gratings within the sample simultaneously for both the partial beams of the further light and the luminescence inhibition light with regard to each other, the light shaping and aligning device may apply the further light and the luminescence inhibition light to the sample one after the other, and it may shift the intensity distributions of the further light and the luminescence inhibition light with regard to each other in between so that the local intensity maxima or the local intensity minima of the further light coincide with the intensity minima of the luminescence inhibition light as desired. In this embodiment of the scanning luminescence light microscope according to the invention, with each change between the further light and the luminescence inhibition light or vice versa, the optical path length of one of the partial beams of each pair of partial beams is varied to adjust the desired relative position of the local intensity maxima or local intensity minima of the further light with regard to the local intensity minima of the luminescence inhibition light.

As already indicated above, the further light often differs from the luminescence inhibition light by its wavelength. Generally, the luminescence inhibition light and the further light may also differ with regard to their intensities. In case of different intensities of a same wavelength, it may be relevant that, in the scanning luminescence light microscope according to the invention, the local intensity maxima of the intensity distribution of the further light can be positioned to coincide with the intensity minima of the intensity distribution of the luminescence inhibition light within the sample.

The scanning luminescence light microscope according to the invention may have separate partial light sources for providing the further light and the luminescence inhibition light, particularly if the wavelengths of the further light and the luminescence inhibition light are different. In another embodiment of the scanning luminescence light microscope according to the invention, the further light and the luminescence inhibition light may be selected from the light of a single light source emitting light at several lines or in a continuous spectrum. Further, light of a light source emitting light of a single wavelength may be converted into light of different wavelengths by shifting its frequency. Thus, the light source may generate or select the further light and the luminescence inhibition light from light of a single starting wavelength or from a starting wavelength distribution emitted by a single partial light source.

The light source of the scanning luminescence light microscope according to the invention may also have partial light sources for each of the non-coherent beams of the further light and the luminescence inhibition light. To avoid the coherence between the beams of the further light and the luminescence inhibition light, it is also possible to use different delays for the different beams whose difference in optical path length is longer than a coherence length of the light source; or the coherence is avoided by other means, like for example by different polarizations or different wavelengths of the partial beams.

Further, the light shaping and aligning device may form the individual line gratings of at least one of the luminescence inhibition light and the further light one after the other within the sample to superimpose them non-coherently to form the overall intensity distribution of the at least one of the luminescence inhibition light and the further light. As long as this formation of the individual line gratings one after the other occurs quickly as compared with registering the luminescence light from the sample for each position of the intensity minima of the luminescence inhibition light, the line gratings formed within the sample one after the other do not have another effect than simultaneously formed line gratings. At least, this applies to one photon processes caused by the respective luminescence inhibition light or further light.

In the scanning luminescence light microscope according to the invention, the light shaping and aligning device may scan the area of interest in the sample in that it varies the relative phases of the coherent partial beams of the further light and of the luminescence inhibition light. If the further light and the luminescence inhibition light are simultaneously applied to the sample so that the optical path lengths from the respective optical grating up to the line grating in the sample have to be simultaneously adjusted for the further light and the luminescence inhibition light, it may, however, be difficult to vary the relative phases of the coherent partial beams for scanning the partial area of interest of the sample without affecting the desired relative positions of the intensity minima or maxima of the further light with regard to the intensity minima of the luminescence inhibition light. In this case, it may be advantageous that the light shaping and aligning device leaves the superimposed intensity distributions of the luminescence inhibition light and the further light unchanged and shifts them together with regard to the sample. Such a shift may, for example, be effected by means of rotating mirrors included in the light shaping and aligning device. The shift may also be effected in that the light shaping and aligning device moves the sample with regard to the objective lens.

As already mentioned above, the further light, in the scanning luminescence light microscope according to the invention, may be excitation light which excites the luminescent marker for the emission of luminescence light, wherein the light shaping and aligning device aligns the intensity distribution of the further light with regard to the intensity distribution of the luminescence inhibition light in such a way that the local intensity maxima of the intensity distribution of the further light coincide with the local intensity minima of the intensity distribution of the luminescence inhibition light. The luminescence inhibition light may, for example, stimulate the luminescent marker for stimulated emission and thus de-excite the excited luminescent marker, or it may transfer or switch the luminescent marker into a dark state in which it is generally not capable of luminescence. In this embodiment of the scanning luminescence light microscope, the luminescence inhibition light may be continuously applied to the sample, whereas the excitation light as the further light is applied to the sample in pulses. In this and any other case of pulsed excitation light as the further light, it is advantageous to register the luminescence light with temporal resolution after each pulse of the excitation light to maximize the spatial resolution and the contrast, as generally known from WO 2012/069076 A1 for an STED scanning luminescence light microscope.

To separately register the luminescence light emitted out of the areas of the individual intensity minima of the intensity distribution of the luminescence inhibition light, a separate detector may be used for each intensity minimum. These detectors may even be non-spatially resolving detectors, like point detectors. Preferably, however, the luminescence light is registered by means of a spatially resolving detector. For enabling a separate registration, it has to be ensured in imaging the luminescence light onto the spatially resolving detector that non-overlapping or at least essentially non-overlapping areas of the detector can be assigned to different measurement areas in the sample including the individual intensity minima. For example, the luminescence light emitted out of the measurement areas including the individual intensity minima may be imaged onto a camera, particularly onto a camera with a sensor array, like for example a CCD or CMOS camera. For assigning the registered luminescence light to the individual intensity minima, the pixels of the camera may be combined to distinct groups, and these distinct groups may be assigned to the different intensity minima.

Figure 1:
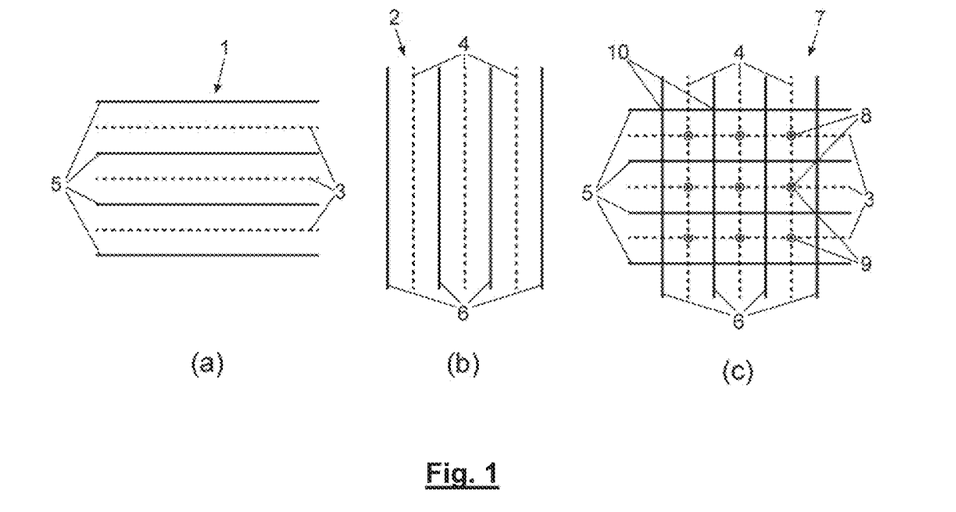
FIG. 1 illustrates two line gratings and their superposition to an intensity distribution.

Referring now in greater detail to the drawings. FIGS. 1 (a) and (b) each show a line grating 1, 2, here consisting of luminescence inhibition light. Each of the line gratings 1 and 2 comprises a plurality of one-dimensionally delimited local intensity minima 3, 4. In the example depicted in FIG. 1, each of the line gratings 1 and 2 comprises three local intensity minima 3, 4. The local intensity minima 3 and the local intensity minima 4 are equidistant and parallel. On both sides, each local intensity minimum 3, 4 is delimited by a local intensity maximum 5, 6, wherein the intensity of the luminescence inhibition light, from the respective local intensity minimum 3, 4, increases towards both delimiting local intensity maxima 5, 6. The luminescence inhibition light of the line grating 1 is not coherent with regard to the luminescence inhibition light of the line grating 1; this fact will also be referred to here by means of indicating that the luminescence inhibition light of the line gratings 1 and 2 is not coherent.

The two line gratings 1 and 2 are superimposed with their local intensity minima 3 and 4 being orthogonal so that they together form an overall intensity distribution 7 depicted in FIG. 1 (c). As the luminescence inhibition light of the two line gratings is not coherent, there is a simple addition of the intensities of the two line gratings 1 and 2 in their superposition. At crossing points 8 in which the local intensity minima 3 and 4 of the line gratings 1 and 2 are crossing, there are local intensity minima 9 which are two-dimensionally delimited by the local intensity maxima 5 and 6. For delimiting the local intensity minima 9 in a third dimension, a further line grating whose local intensity minima are orthogonal to both local intensity minima 3 and 4 may additionally be superimposed.

In the intensity distribution 7 depicted in FIG. 1 (c), each of the three local intensity minima 3 of the line grating 1 is superimposed with each of the three local intensity minima 4 of the line grating 2 so that the resulting intensity distribution 7 has a total of nine crossing points 8 and thus also has nine local intensity minima 9. The local intensity minima 3 and 4 are zero points in which the intensity of the luminescence inhibition light, in an ideal case, completely disappears. Then, the intensity of the luminescence inhibition light then also completely disappears in the two-dimensionally delimited local intensity minima 9.

Corresponding to the equidistant arrangement of the local intensity minima 3 and 4, wherein the distances of the local intensity minima 3 and 4 in both line gratings 1 and 2, i.e. the grating constants of both line gratings 1 and 2 are the same, the local intensity minima 9 of the intensity distribution 4 are arranged in a square raster. If the local intensity maxima 5 and 6 of both the line gratings 1 and 2 have same maximum intensities, each of the local intensity minima 9, in the direction of the one-dimensionally delimited local intensity minima 3 and 4, is delimited by one of the local intensity maxima 5 and 6 at this maximum intensity. In a direction diagonal with regard to the local intensity minima 3, 4, the intensities of the local intensity maxima 5 and 6 add up in their crossing points 10 to twice this maximum intensity. This strictly applies to simultaneously applied line gratings 1 and 2 of luminescence inhibition light. An equal effect may also be achieved with shortly consecutive line gratings 1 and 2. Also in this case, twice the amount of light is applied to the crossing points 10 as compared to the areas of the individual local intensity maxima 5 and 6 of the line gratings 1 and 2. As a result, at least with regard to an effect of the luminescence inhibition light based on a one photon process, a same distribution of a transfer effect of the luminescence inhibition light around the local intensity minima 9 is achieved.

Figure 2:
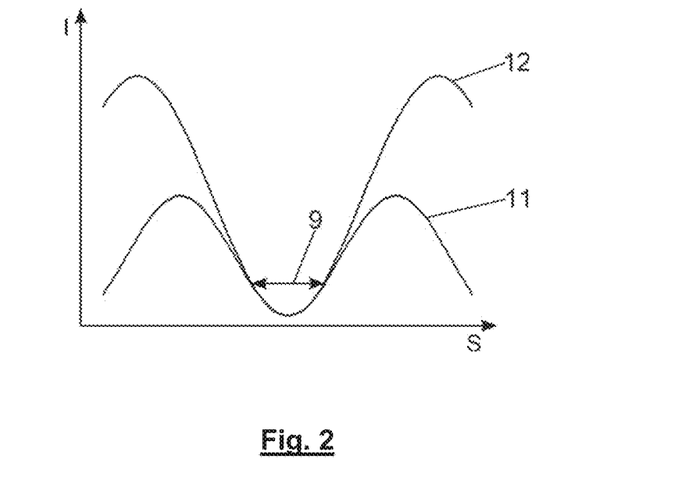
FIG. 2 shows the intensity distribution according to FIG. 1 in sections along different directions.

FIG. 2 depicts a course 11 of the intensity distribution 7 in a section across the one-dimensionally delimited local intensity minima 3, 4. For direct comparison, a course 12 of the intensity distribution 7 in a section diagonal to the one-dimensionally delimited local intensity minima 3 and 4 is depicted. The courses 11 and 12 each indicate an intensity I of the luminescence inhibition light over a space coordinate S.

As may be seen from FIG. 2, the course 12 as compared to the course 11, in the crossing points 10 of the local intensity maxima 5 and 6, displays twice the maximum intensity. The crossing points 10, however, are farther away from the center of the local intensity minimum 9 than the local intensity maxima 5 or 6 on the course 11. Thus, with both courses 11 and 12, a saturation intensity defining the dimensions of the local intensity minimum 9 is reached at a same distance to the center of the local minimum 9. Whereas the courses 11 and 12 differ outside the local minimum 9, their differences within and at the border of the local minimum 9 are negligible. As a result, the local intensity minima 9 of the intensity distribution 7 are essentially circular.

The fact that the local intensity minima of the intensity distribution are essentially circular, if two orthogonal line gratings with a sine-shaped intensity course of same grating constants or period length are superimposed, may also be seen from the following considerations:

The intensity distribution I(x,y) resulting from the superposition of two orthogonal sine-shaped line gratings having an amplitude $I_0$ and a period l is given by $$I(x, y) = I_0 \sin^2\left(\frac{2\pi x}{l}\right) + I_0 \sin^2\left(\frac{2\pi y}{l}\right),$$

wherein x and y are the space coordinates predetermined by the structuring of the two line gratings. In a method based on the RESOLFT concept, one may directly deduce an effective point spread function from the intensity distribution I(x,y) of the luminescence inhibition light. This effective point spread function $h_{eff}$ is given by $$h_{\it{eff}}(x,y) = \left(1 + \frac{I(x,y)}{I_S}\right)^{-1} = \left(1 + \frac{I_0}{I_S}\left[\sin^2\left(\frac{2\pi x}{l}\right) + \sin^2\left(\frac{2\pi y}{l}\right)\right]\right)^{-1}$$

wherein $I_S$ designates the saturation intensity of the luminescence inhibition light at which half of the luminescent marker in the area of the maximum amplitude of the intensity course is transferred into the second state. For high intensities $I_0$ as compared to $I_S$, a non-disappearing value only remains for small values of x and y. Correspondingly, the effective point spread function may be approximated by means of the following Taylor expansion $$h_{\it{eff}}(x,y) = 1 - \frac{4I_0\pi^2}{I_S l^2}x^2 - \frac{4I_0\pi^2}{I_S l^2}y^2 + 2\left(\frac{4I_0\pi^2}{I_S l^2}\right)^2 x^2 y^2 + O(x^4) + O(y^4)$$

$$\approx 1 - \frac{I_0}{I_S}\omega^2 x^2 - \frac{I_0}{I_S}\omega^2 y^2$$

$$= 1 - \frac{I_0}{I_S}r^2$$

with a radial frequency $\omega=2\pi/l$ of the resulting intensity distribution and a radial coordinate r corresponding to a distance to the center of the local minimum of the intensity distribution. The full width at half maximum $\Delta r$ of the local minimum of the resulting intensity distribution is $$\Delta r = \frac{l}{2\pi}\sqrt{\frac{2I_S}{I_0}}.$$

All at all, there is an approximately radial symmetric local minimum whose extensions depend on the ratio of the saturation intensity and the amplitude of the line grating as well as on a period of the line grating.

In a scanning luminescence light microscope according to the invention, not only the luminescence inhibition light is structured. Instead, also further light which is used in the scanning luminescence light microscope and which differs from the luminescence inhibition light is structured in the area of the respective sample. For this purpose, at least one line grating is also formed of the further light, and preferably several such line gratings are formed and superimposed in such a way that their respective parallel intensity maxima and intensity minima are crossing orthogonally. If the further light, for example, is excitation light, intensity maxima result at the crossing points of the one-dimensionally delimited intensity maxima of its line gratings, which are two-dimensionally delimited by the superimposed local intensity minima of the line gratings and in which a luminescent dye in the respective sample is excited to a maximum extent. These intensity maxima are aligned such as to coincide with the intensity minima of the intensity distribution of the superimposed line gratings of the luminescence inhibition light as described in the following example.

Figure 3:
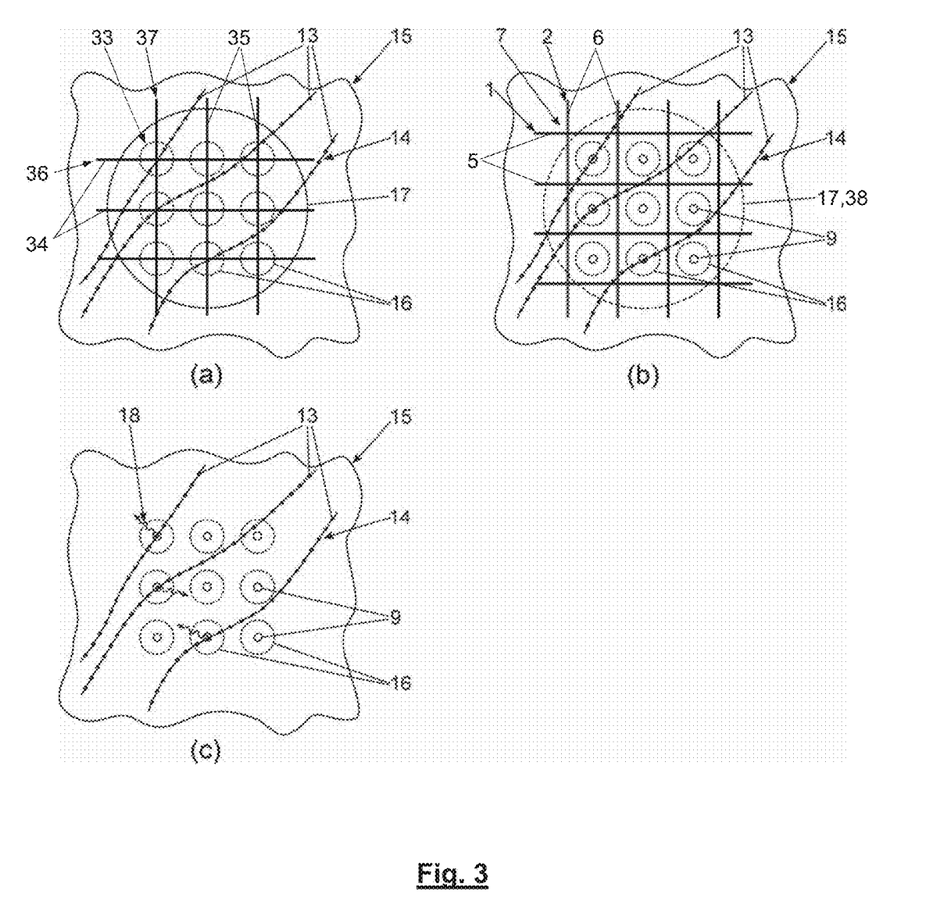
FIG. 3 illustrates methods steps of a method of spatial high resolution imaging a structure of a sample marked with a luminescent marker.

FIGS. 3 (a) to (c) show steps in spatial high resolution imaging a structure 14 of a sample 15, the structure comprising a luminescent marker 13. In the step depicted in FIG. 3 (a), the sample, in an area of interest, is simultaneously subjected to a plurality of two-dimensionally delimited local intensity maxima 16 of an intensity distribution 33 of excitation light 17 exciting the luminescent marker 13 into a luminescent state out of which the luminescent marker 13 may return into its ground state under emission of luminescence light 18. The two-dimensional delimited local intensity maxima 16 of the intensity distribution 33 are formed at the crossing points of one-dimensional delimited intensity maxima 34 and 35 of two line gratings 36 and 37 of the excitation light which are orthogonally superimposed in the sample 15 in a similar way as depicted in FIG. 1 for the luminescence inhibition light.

According to FIG. 3 (b), the sample 15, in addition to the intensity distribution 33 of the excitation light 17, is subjected to the intensity distribution 7 of the luminescence inhibition light 38 which is generated by the superposition of the two line gratings 1 and 2 according to FIG. 1. Each of the uniform two-dimensionally delimited local intensity minima 9 of the intensity distribution 7 is at the place of one of the intensity maxima 16. When subjecting the sample 15 to the luminescence inhibition light 38, the luminescent marker 13, everywhere outside the local intensity minima 9 of the intensity distribution 7 of the luminescence inhibition light 38, is transferred out of is excited luminescent state back into its electronic ground state without the emission of luminescence light 18. Thus, after the step according to FIG. 3 (b), the luminescent marker 13 is still in its luminescent state only within the areas of the sample 15 determined by the local intensity minima 9.

In the method step depicted in FIG. 3 (c), the luminescence light 18 emitted out of each of the intensity minima 9 is spatially separately registered. Even if the spatial resolution in registering the luminescence light 18 is not better than that one in forming the intensity maxima 16 of the excitation light, the luminescence light 18 separately registered for each intensity minimum 9 can be assigned to the position of this intensity minimum 9 as the emitted luminescence light 18 may only come out of the area of this intensity minimum 9.

In scanning the sample with the intensity minima 9, the steps depicted in FIG. 3 are repeated for different locations of the local intensity minima 9 within the sample. In this way, a concentration distribution of the luminescent marker 13 in the sample 15 is determined, and, thus, the structure 14 is imaged. As the sample 15 is not only scanned with a single measurement area or intensity minimum 9 of the luminescence inhibition light 38 but simultaneously with a plurality of measurement areas or intensity maxima 16, scanning of a larger area of the sample 15 and thus imaging the structure 14 in this area is considerably accelerated. In the case depicted in FIG. 3, the time for scanning the sample is, for example, reduced to a ninth part of the time which would be required when using an intensity distribution of the luminescence inhibition light only having one local minimum.

Figure 4:
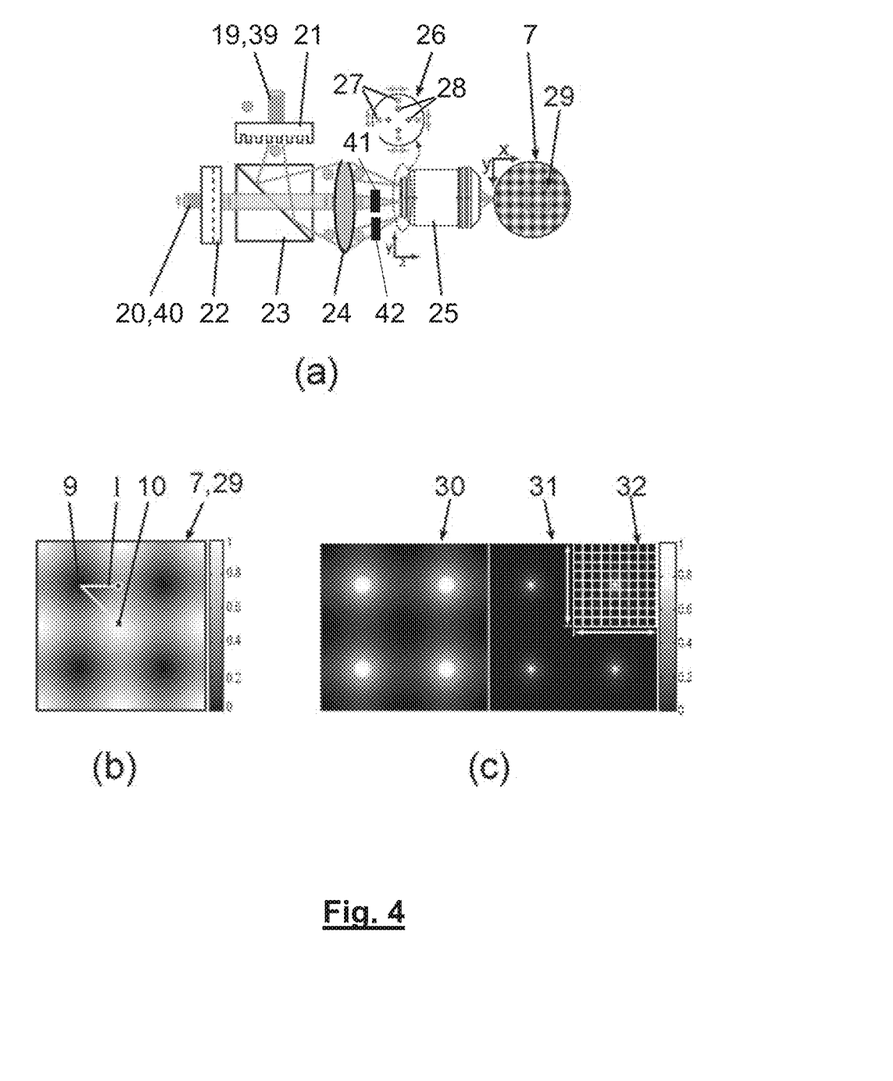
FIG. 4 illustrates an intensity distribution resulting from the superposition of two line gratings and an effective point spread function resulting from this intensity distribution.

FIG. 4 (a) schematically depicts how the above described orthogonal sine-shaped line gratings may be generated and superimposed to form the intensity distribution 7 of the luminescence inhibition light 38 described by the function I(x,y) and to form the intensity distribution 33 of the excitation light 17 offset thereto in both direction x and y by half a grating constant. For generating the line gratings 1 and 2, and 36 and 37, two pairs of beams 19 and 39, and 20 and 40 of orthogonally polarized beams pass through one of two orthogonally arranged optical gratings 21, 22. The beams 19 and 20 are beams of the luminescence inhibition light 38, and they are orthogonally polarized with regard to each other in a same way as the beams 20 and 40 of the excitation light 17. Each beam 19, 20, 39, 40, by means of the respective optical grating 21, 22, is split up into partial beams. Only those of these partial beams which correspond to the first order diffraction maxima are used. All partial beams used are then brought together and focused by a lens 24 into the back aperture of an objective lens 25. An intensity distribution of the luminescence inhibition light and the excitation light in the back aperture of the objective 25, which is strongly schematic depicted in a detail 26, comprises four symmetrically arranged focuses 27 and 28 with polarizations as indicated by arrows. Those pairs of focuses 27 on opposite sides of the center of the back aperture correspond to the first order diffraction maxima of the beams 19, of the luminescence inhibition light of the respective polarization. Correspondingly, the pairs of focuses 28 on opposite sides of the center of the back aperture correspond to the first order diffraction maxima of the beams 39, 40 of the excitation light with the respective polarizations. In the present case, the focuses 28 are closer together than the focuses 27. This corresponds to a smaller deviation or deflection angle of the beams 39 and 40 at the optical gratings 21 and 22 as compared to the beams 19 and 20 due to the shorter wavelength of the excitation light.

By projecting the two partial beams of all beams 19, 20, 39 and 40 into the sample, the line gratings are formed and superimposed in the focal plane of the objective 25. This superposition generates the intensity distribution 7 of the luminescence inhibition light displaying the intensity course according to the function I(x,y). In FIG. 4 (a) the intensity distribution 33 of the excitation light which is formed from the beams 39 and 40 is not separately depicted. This intensity distribution 33 is complementary with regard to the intensity distribution 7 in so far as in each local intensity minimum of the intensity distribution 7 a local intensity maximum of the non-depicted intensity distribution 33 is located. Despite different wavelengths of the excitation light and the luminescence inhibition light, the grating constants of the line gratings forming the intensity distributions 7 and 33 are equal, because the grating constants depend on the quotient of the angle of the respective partial beam and of its wavelength and because the optical gratings 21 and 22 previously had a complementary effect on the angle of the partial beams depending on their wavelength. The relative position of the intensity maxima of the excitation light with regard to the intensity minima of the luminescence inhibition light is adjusted by means of optical elements 41 and 42 which are each arranged in one of the partial beams of each of the beams 19, 20, 39 and 40. By means of these optical elements 41 and 42, the parallel intensity maxima of one of the line gratings of the excitation light and the parallel intensity minima of one of the line gratings of the luminescence inhibition light are brought to coincide in that the optical path lengths between the optical gratings 21, 22 up to the focal plane of the objective 25 are adjusted with regard to each other. The optical elements 41 and 42 may, for example, be made of highly refractive material by which the optical path lengths for the passing partial beams are elongated. This does not only result in a collective movement of the parallel intensity maxima and intensity minima of the line gratings generated by means of the same optical grating 21 or 22 from the excitation light and the luminescence inhibition light but also in a relative shift of the intensity maxima of the excitation light with regard to intensity minima of the luminescence inhibition light. This is due to the fact that same changes of the absolute optical path lengths, due to the different wavelengths of the excitation light and the luminescence inhibition light, have different effects on the relative phases between the partial beams of the respective beams 19, 20 or 39, 40.

In FIG. 4 (b), the intensity distribution 7 in the focus plane is depicted in an enlarged detail 29 showing four two-dimensionally delimited local intensity minima 9. The local intensity minima 9 are about circular, wherein their radius is about half the period or grating constant l of the line gratings.

In FIG. 4 (c), for example, two effective point spread functions 30, 31 belonging to the intensity distribution 7 and corresponding to the detail depicted in FIG. 4 (b) are shown. In a first approximation, the effective point spread functions 30, 31 may each be described by the function $h_{eff}$. In the effective point spread function 30 depicted on the left hand side of FIG. 4 (c), the ratio of $I_0$ to $I_S$ is five. Thus, the point spread function 30 has four circular local maxima of a full width at half maximum of $$\Delta r = \frac{l}{\sqrt{10}\,\pi}$$

corresponding to the local intensity minima 9. Each maximum and its full width at half maximum determine the area of the sample to which the measurement signal, i.e. the luminescence light emitted by the luminescent marker located in the associated measurement area or local intensity minimum may be assigned. In the point spread function 31 depicted on the right hand side of FIG. 4 (c), the ratio of $I_0$ to $I_S$ is 100. Consequently, the full width at half maximum is reduced to $$\Delta r = \frac{l}{\sqrt{200}\,\pi}.$$

Thus, the measurement signal may be assigned to a smaller area within the sample, i.e. an enhanced spatial resolution is achieved. For depicting the structure, the sample is, for example, scanned according to the raster 32, wherein the measurement signal obtained for each position is assigned to one pixel of the raster 32.

Figure 5:
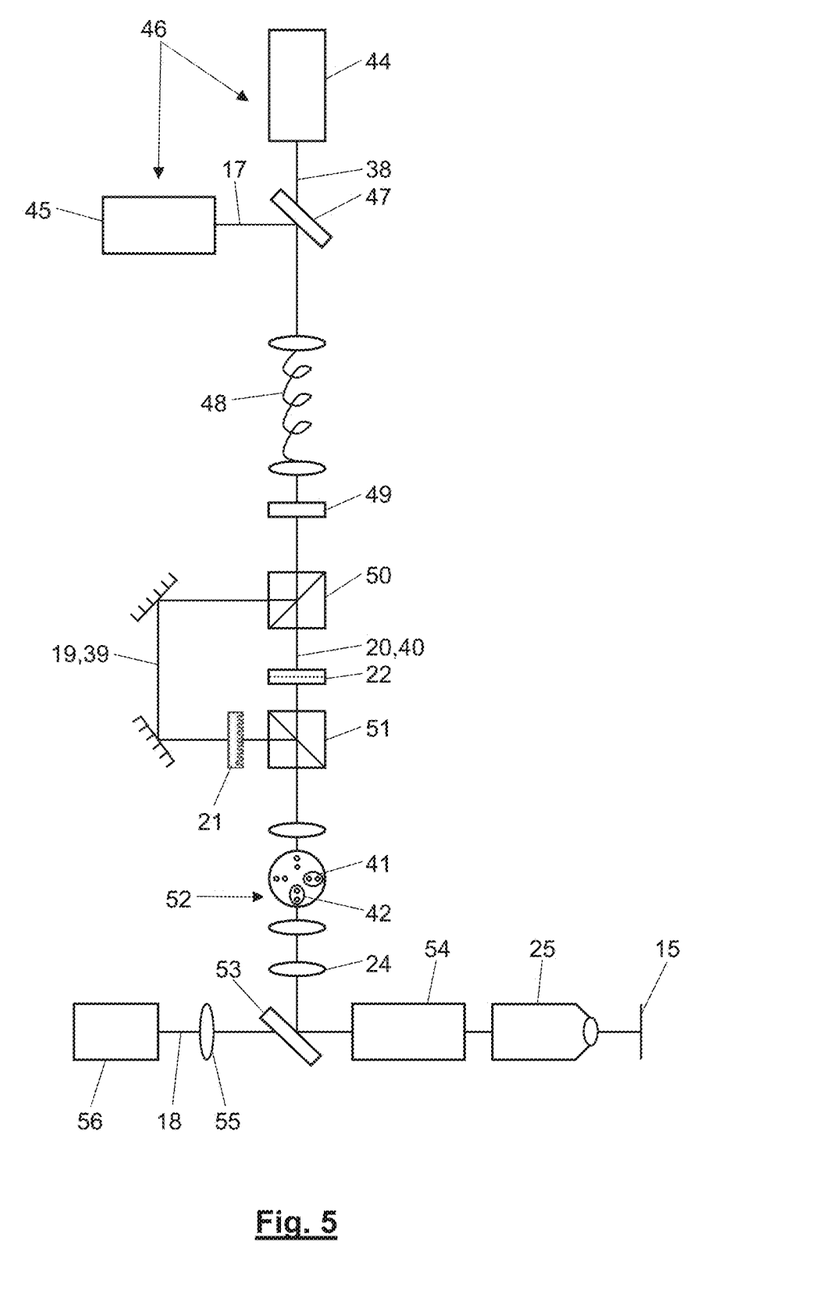
FIG. 5 illustrates a scanning luminescence light microscope for spatial high resolution imaging a structure of a sample marked with a luminescent marker.

In FIG. 5, an embodiment example of a scanning luminescence light microscope 43 according to the invention for spatially high resolution imaging a structure of a sample 15 marked with a luminescent marker is depicted in a strongly schematized way. The luminescence inhibition light 38 is provided by a partial light source 44 of a light source 46, and the excitation light 17 is provided by a partial light source 45 of the light source 46. By means of a dichroitic beam splitter 47, the luminescence inhibition light 38 and the excitation light 17 are merged. An optical fiber 48 with associated fiber optics serves for beam filtration, and a λ/2 plate 49 which is active both for the wavelength of the luminescence inhibition light 38 and the wavelength of the excitation light 17 serves for rotation of the light polarization. By means of a polarizing beam splitter 50, the luminescence inhibition light 38 and the excitation light 17 are both split up into the beams 19 and 20, and 39 and 40 of orthogonal polarizations, respectively. The beams 19 and 39, or 20 and 40 then together pass one of the two optical gratings 21, 22. By means of a further polarizing beam splitter 51, the beams 19 and 20, and 39 and 40 are merged again. After passing through an optic 52 selecting the first order diffraction maxima, in which the optical elements 41 and 42 are arranged, the beams 19, 20 and 39, 40 are projected via a further dichroitic beam splitter 53, via a beam deflection device 54 and via the objective lens 25 into the sample 15. By means of projecting the beams 19, 20, in the focus plane of the objective lens 25 the two line gratings of one-dimensional delimited intensity minima of the luminescence inhibition light are generated and superimposed. This superposition of the line gratings of the luminescence inhibition light results in the intensity distribution comprising a plurality of two-dimensionally delimited local intensity minima. By means of projecting the beams 39, 40, in the focal plane of the objective lens 25 the two line gratings with the one-dimensionally delimited intensity maxima of the excitation light are generated and superimposed. This superposition of the line gratings of the excitation light results in the intensity distribution comprising a plurality of two-dimensionally delimited local intensity maxima. By means of the optical elements 41 and 42, the relative phases of the partial beams are adjusted with regard to each other in such a way that a two-dimensional delimited local intensity maximum of the excitation light coincides with a two-dimensionally delimited local intensity minimum of the luminescence inhibition light.

The luminescence light 18 emitted out of the sample 15 is selectively transmitted by a dichroitic beam splitter 53 and imaged onto a camera 56 by a lens 55 arranged behind the dichroitic beam splitter 53. The camera 56 separately registers the luminescence light for each of the intensity minima of the intensity distribution of the luminescence inhibition light and for each position of each of these intensity minima while an area of interest of the sample 15 is scanned with these intensity minima by means of the scanning device 54. Scanning may be limited to that partial area of the area of interest of the sample 15 which, in a starting position, is located between neighboring intensity minima.

The light shaping and aligning device of the scanning luminescence light microscope 43 according to the present invention depicted in FIG. 5 includes all its components except of the light source 46 and the camera 56 with the lens 55.

Many variations and modifications may be made to the preferred embodiments of the invention without departing substantially from the spirit and principles of the invention. All such modifications and variations are intended to be included herein within the scope of the present invention, as defined by the following claims.

We claim:

1. A scanning luminescence light microscope for spatial high resolution imaging a structure in a sample, the structure comprising a luminescent marker, the microscope comprising
    a light source configured to provide luminescence inhibition light and further light differing from the luminescence inhibition light;
    a light shaping and aligning device including an objective lens and configured to form, from two non-coherent beams of the luminescence inhibition light, by means of two optical gratings, two pairs of coherent partial beams of the luminescence inhibition light and to focus and superimpose the two pairs of partial beams of the luminescence inhibition light by means of the objective so that the two pairs of partial beams of the luminescence inhibition light form two crossing line gratings of the luminescence inhibition light in the area of the sample, each of the two crossing line gratings of the luminescence inhibition light comprising a plurality of intensity minima delimited in one direction so that an intensity distribution of the luminescence inhibition light in the sample comprises a two-dimensional array of local intensity minima which are delimited in at least two directions,
    wherein at least one beam of the further light enters the light shaping and aligning device together with one of the two beams of the luminescence inhibition light so that the light shaping and aligning device, from the at least one beam of the further light, by means of one of the optical gratings, forms two coherent partial of the further light and focuses and superimposes the partial beams of the further light by means of the objective so that the partial beams of the further light form a line grating of the further light in the area of the sample which comprises a plurality of intensity maxima delimited in one direction and intensity minima extending in parallel to the local intensity minima of one of the line gratings of the luminescence inhibition light;
    wherein the light shaping and aligning device is configured to align the line grating of the further light with regard to the one of the line gratings of the luminescence inhibition light in such a way that the local intensity maxima or the local intensity minima of the further light coincide with the intensity minima of the luminescence inhibition light;
    wherein the light shaping and aligning device is configured to move the intensity distributions of the further light and the luminescence inhibition light with regard to the sample to scan an area of interest of the sample with the intensity minima of the intensity distribution of the luminescence inhibition light; and
    a detector configured to register the luminescence light emitted out of the individual intensity minima of the intensity distribution of the luminescence inhibition light separately for each of the intensity minima and for each position of each of the intensity minima within the sample.

2. The microscope of claim 1,
    wherein the at least one beam and a second non-coherent beam of the further light enter the light shaping and aligning device, each together with one of the two beams of the luminescence inhibition light, so that the light shaping and aligning device, from the at least one beam and the second non-coherent beam of the further light, by means of the optical gratings, forms two pairs of coherent partial beams of the further light and focuses and superimposes the two pairs of coherent partial beams of the further light by means of the objective so that the two pairs of coherent partial beams of the further light form two crossing line gratings of the further light in the area of the sample, each of the two crossing line gratings of the further light comprising a plurality of intensity maxima delimited in one direction and intensity minima extending in parallel to the local intensity minima of one of the line gratings of the luminescence inhibition light so that an intensity distribution of the further light in the sample comprises a two-dimensional array of local intensity maxima and local intensity minima which are each delimited in at least two directions; and
    wherein the light shaping and aligning device is configured to align the intensity distribution of the further light with regard to the intensity distribution of the luminescence inhibition light in such a way that the local intensity maxima or the local intensity minima of the further light coincide with the local intensity minima of the intensity distribution of the luminescence inhibition light.

3. The microscope of claim 1, wherein the light shaping and aligning device is configured to adjust optical path length of the partial beams of each pair of coherent partial beams of the further light and optical path lengths of the partial beams of the pair of partial beams of the luminescence inhibition light formed by means of the same optical grating in such a way that the local intensity maxima or the local intensity minima of the further light coincide with the local intensity minima of the intensity distribution of the luminescence inhibition light.

4. The microscope of claim 3, wherein the optical path lengths extend from the respective optical grating to the respective line grating of the further light and the luminescence inhibition light.

5. The microscope of claim 3, wherein the light shaping and aligning device comprises at least one optical element which is selectively arranged in one or both of
- a partial beam of one of the pairs of the coherent partial beams of the further light and
- one of the partial beams of the pair of the partial beams of the luminescence inhibition light formed by means of the same optical grating as the one of the pairs of the coherent partial beams of the further light.

6. The microscope of claim 5, wherein the optical element is interchangeable.

7. The microscope of claim 5, wherein the optical element is selected from the group of chromatic and birefringent optical elements.

8. The microscope of claim 5, wherein the optical element, for different wavelengths of at least one of the further light and the luminescence inhibition light, adjusts the optical path lengths of the partial beams of each pair of coherent partial beams of the further light and the optical path lengths of the partial beams of the pair of the coherent partial beams of the luminescence inhibition light formed by means of the same optical gratings with regard to each other in such a way that the local intensity maxima or the local intensity minima of the line gratings of the further light coincide with the parallel local intensity minima of the respective line grating of the luminescence inhibition light.

9. The microscope of claim 8, wherein the optical path lengths extend from the respective optical grating to the respective line grating of the further light and the luminescence inhibition light.

10. The microscope of claim 1, wherein the light shaping and aligning device is configured to apply the further light and the luminescence inhibition light to the sample one after the other and shifts the intensity distributions of the luminescence inhibition light and the further light with regard to each other in the meanwhile in such a way that the local intensity maxima or the local intensity minima of the intensity distribution of the further light coincide with the local intensity minima of the intensity distribution of the luminescence inhibition light.

11. The microscope of claim 1, wherein the luminescence inhibition light and the further light differ with regard to at least one of their wavelengths and their intensities.

12. The microscope of claim 1, wherein the light source comprises separate partial light sources for providing the further light and the luminescence inhibition light.

13. The microscope of claim 12, wherein the light source comprises separate partial light sources for each of the non-coherent beams of the further light and the luminescence inhibition light.

14. The microscope of claim 1, wherein the light source is configured to generate the further light and the luminescence inhibition light from light of one starting wavelength.

15. The microscope of claim 1, wherein the light source is configured to select the further light and the luminescence inhibition light from a starting wavelength distribution.

16. The microscope of claim 1, wherein the light shaping and aligning device is configured to form the individual line gratings of at least one of the luminescence inhibition light and the further light one after the other in the sample to non-coherently superimpose them to the intensity distribution of at least one of the luminescence inhibition light and the further light.

17. The microscope of claim 1, wherein the light shaping and aligning device is configured to scan the sample in that it varies relative phases of the coherent partial beams of the further light and the luminescence inhibition light.

18. The microscope of claim 1, wherein the light shaping and aligning device is configured to scan the region of interest of the sample in that it shifts the superimposed intensity distributions of the luminescence inhibition light and the further light together with regard to the sample.

19. A scanning luminescence light microscope for spatial high resolution imaging a structure in a sample, the structure comprising a luminescent marker, the microscope comprising
- a light source configured to provide luminescence inhibition light and excitation light differing from the luminescence inhibition light and exciting the luminescence marker for emission of luminescence light;
- a light shaping and aligning device including an objective lens and configured to form, from two non-coherent beams of the luminescence inhibition light, by means of two optical gratings, two pairs of coherent partial beams of the luminescence inhibition light and to focus and superimpose the two pairs of partial beams of the luminescence inhibition light by means of the objective so that the two pairs of partial beams of the luminescence inhibition light form two crossing line gratings of the luminescence inhibition light in the area of the sample, each of the two crossing line gratings of the luminescence inhibition light comprising a plurality of intensity minima delimited in one direction so that an intensity distribution of the luminescence inhibition light in the sample comprises a two-dimensional array of local intensity minima which are delimited in at least two directions,
- wherein two non-coherent beams of the excitation light enter the light shaping and aligning device, each together with one of the two beams of the luminescence inhibition light, so that the light shaping and aligning device, from the two non-coherent beams of the excitation light, by means of the optical gratings, forms two pairs of coherent partial beams of the excitation light and focuses and superimposes the two pairs of coherent partial beams of the excitation light by means of the objective so that the two pairs of coherent partial beams of the excitation light form two crossing line gratings of the excitation light in the area of the sample, each of the two crossing line gratings of the excitation light comprising a plurality of intensity maxima delimited in one direction and intensity minima extending in parallel to the local intensity minima of one of the line gratings of the luminescence inhibition light so that an intensity distribution of the excitation light in the sample comprises a two-dimensional array of local intensity maxima and local intensity minima which are each delimited in at least two directions;

wherein the light shaping and aligning device is configured to align the intensity distribution of the excitation light with regard to the intensity distribution of the luminescence inhibition light in such a way that the local intensity maxima of the excitation light coincide with the local intensity minima of the intensity distribution of the luminescence inhibition light;

wherein the light shaping and aligning device is configured to move the intensity distributions of the excitation light and the luminescence inhibition light with regard to the sample to scan an area of interest of the sample with the intensity minima of the intensity distribution of the luminescence inhibition light; and a detector configured to register the luminescence light emitted out of the individual intensity minima of the intensity distribution of the luminescence inhibition light separately for each of the intensity minima and for each position of each of the intensity minima within the sample.

20. The microscope of claim 1, wherein the further light is excitation light exciting the luminescence marker for emission of luminescence light, wherein the light shaping and aligning device is configured to align the intensity distribution of the further light with regard to the intensity distribution of the luminescence inhabitation light in such a way that the local intensity maxima of the intensity distribution of the further light coincide with the local intensity minima of the intensity distribution of the luminescence inhibition light.

* * * * *